United States Patent [19]

Miyano et al.

[11] Patent Number: 5,756,797
[45] Date of Patent: May 26, 1998

[54] PROCESS FOR PREPARING TRIBROMONEOPENTYL CHLOROALKYL PHOSPHATES

[75] Inventors: Nobutaka Miyano, Handa; Noriaki Tokuyasu, Ikoma, both of Japan

[73] Assignee: Daihachi Chemical Industry Co., Ltd., Osaka, Japan

[21] Appl. No.: 859,263

[22] Filed: May 20, 1997

[30] Foreign Application Priority Data

May 22, 1996 [JP] Japan ................... 8-127059

[51] Int. Cl.$^6$ ................................................. C07F 9/09
[52] U.S. Cl. ................................. 558/99; 558/100
[58] Field of Search ........................... 558/99, 100

[56] References Cited

U.S. PATENT DOCUMENTS

| | | |
|---|---|---|
| 3,707,586 | 12/1972 | Turley . |
| 3,803,272 | 4/1974 | Pivawer et al. . |
| 4,046,719 | 9/1977 | Stanaback et al. . |
| 4,083,825 | 4/1978 | Albright et al. . |
| 5,627,299 | 5/1997 | Tokuyasu et al. . |

FOREIGN PATENT DOCUMENTS

| | | |
|---|---|---|
| 0735039 | 10/1996 | European Pat. Off. . |
| 49-62424 | 6/1974 | Japan . |
| 61-3797 | 2/1986 | Japan . |
| 7-21086 | 3/1995 | Japan . |
| 1583404 | 1/1981 | United Kingdom . |

Primary Examiner—Michael G. Ambrose
Attorney, Agent, or Firm—Greenblum & Bernstein P.L.C.

[57] ABSTRACT

A process of preparing a tribromoneopentyl chloroalkyl phosphate of the formula (3):

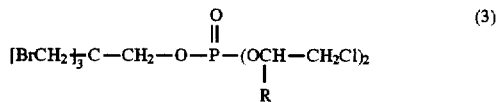

, wherein R is hydrogen atom, an alkyl or chloroalkyl group. The process includes three steps: In the first step, an alkylene oxide is reacted with phosphorus trichloride in a chemical equivalent or less amount to the alkylene oxide to obtain a tris(chloroalkyl) phosphite of the formula (1):

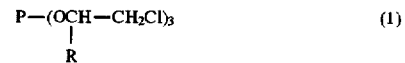

, wherein R is the same as defined above. In the second step, the tris(chloroalkyl) phosphite is reacted with chlorine to obtain a bis(chloroalkyl) phosphorochloridate of the formula (2):

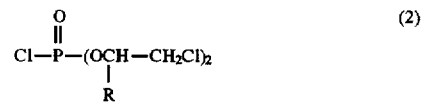

, wherein R is the same as defined above. And in the third step, the bis(chloroalkyl) phosphorochloridate is reacted with tribromoneopentyl alcohol.

20 Claims, No Drawings

PROCESS FOR PREPARING TRIBROMONEOPENTYL CHLOROALKYL PHOSPHATES

BACKGROUND OF THE INVENTION

1. Field of the Invention

The present invention relates to a process for preparing tribromoneopentyl chloroalkyl phosphates. Particularly, it relates to a process for preparing tribromoneopentyl chloroalkyl phosphates which can be used as flame-retardant for polyurethane foams to provide flame retardancy, low fogging characteristic, resistance to scorching and resistance to discoloration at high temperatures and can show resistance to hydrolysis so that they hardly release free halogen.

2. Description of Related Art

Polyurethanes, which are typical thermosetting resins, and their foams are widely used in manufacture of various kinds of daily products including automobile parts because they can be obtained at relatively low costs and have remarkable characteristics such as good moldability. However, polyurethane foams are combustible and tend to cause uncontrollable combustion once they catch fire. Various of efforts have been made in this industry for flame-retarding polyurethane foams. Today in some fields using polyurethane foams such as automobile interior furnishing, the flame-retardancy is legally required. Also, although environmental preservation is socially highlighted and dioxin (halodibenzodioxins) and CFC (chlorofluoro carbon) problems are zealously discussed, low fogging characteristic and resistance to discoloration at high temperatures in addition to flame retardancy are critical issues in the manufacture of automobile parts using polyurethane foams.

In order to give flame-retardancy to polyurethane foams, for example, tribromoneopentyl chloroalkyl phosphates provided by U.S. Pat. Nos.4,046,719, 4,083,825 and Japanese Patent Publication No. Sho61(1986)-3797 are conventionally added. However, the tribromoneopentyl chloroalkyl phosphates obtained by the methods disclosed in the above-mentioned patents contain, in addition to the desired flame-retardant tribromoneopentyl bis(chloroalkyl) phosphates, about 10 wt % tris(chloroalkyl) phosphates which are monomeric components, about 20 wt % bis(tribromoneopentyl) chloroalkyl phosphates and about 5 wt % tris (tribromoneopentyl) phosphate which are crystalline components.

When the tribromoneopentyl chloroalkyl phosphate is used as flame-retardant, it is desirable that the content of the monomeric components is as low as possible since the monomeric components easily volatilize by heat and thus adversely affect low fogging characteristic.

On the other hand, the crystalline bis(tribromoneopentyl) chloroalkyl phosphate and tris(tribromoneopentyl) phosphate affect the viscosity of a resinous product, producing bad effects on its workability due to high viscosity and solidification.

As a process of preparing a phosphoric ester from phosphorus trichloride, U.S. Pat. No. 3,707,586 and Japanese Unexamined Patent Publication No. Sho49(1974)-62424 disclose processes for preparing a tetrakis(2-haloalkyl) alkylene diphosphate. According to the processes, phosphorus trichloride is reacted with ethylene oxide to produce tris(2-chloroethyl) phosphite, which is then reacted with chlorine gas to produce bis(2-chloroethyl) phosphorochloridate and ethylene dichloride. And the reaction product is reacted with ethylene glycol to produce the object phosphoric ester.

Japanese Patent Publication No. Hei7(1995)-21086 discloses a process for preparing a halogenated alkyl phosphate from phosphorus trichloride and neopentyl glycol. According to this process, phosphorus trichloride is reacted with neopentyl glycol to produce a cyclic phosphorus compound, which is then reacted with bromine to produce a halogenated phosphate by cleavage of the cyclic phosphorus compound. The halogenated phosphate is then reacted with ethylene oxide to produce the desired halogenated alkyl phosphate.

However, these phosphates obtained by the above-mentioned two methods are not satisfactory in low fogging characteristic, resistance to discoloration at high temperatures and resistance to hydrolysis. Nor is the free halogen released from the phosphates well controlled. Before the present invention, it is believed that there are no process known for preparing tribromoneopentyl chloroalkyl phosphates satisfying these requirements.

The present inventors previously found a process for preparing a tribromoneopentyl chloroalkyl phosphate with high purity wherein phosphorus oxychloride is reacted with tribromoneopentyl alcohol in first reaction and then the ester obtained in the first reaction is reacted with an alkylene oxide in second reaction.

SUMMARY OF THE INVENTION

Under these circumstances, the present inventors aim to provide a tribromoneopentyl chloroalkyl phosphate which is less contaminated with monomeric and/or crystalline components, thereby showing good flame retardancy and low fogging characteristic for polyurethane foams.

However, the inventors have found from keen study that tribromoneopentyl chloroalkyl phosphates with much higher purity can be obtained by the following process and have achieved the present invention.

Accordingly, the present invention provides a process for preparing a tribromoneopentyl chloroalkyl phosphate of the formula (3):

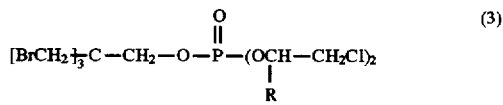

, wherein R is hydrogen atom, an alkyl or chloroalkyl group, comprising;

a first step of reacting an alkylene oxide with phosphorus trichloride in a chemical equivalent or less amount to the alkylene oxide to obtain a tris(chloroalkyl) phosphite of the formula (1):

, wherein R is the same as defined above;

a second step of reacting the tris(chloroalkyl) phosphite with chlorine to obtain a bis(chloroalkyl) phosphorochloridate of the formula (2):

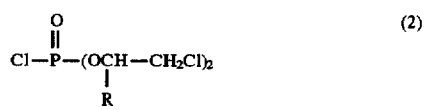

, wherein R is the same as defined above; and a third step of reacting the bis(chloroalkyl) phosphorochloridate with tribromoneopentyl alcohol.

Examples of R in the formulas (1) to (3) are hydrogen atom, a straight-chain and branched-chain alkyl group having 1 to 10 carbon atoms such as methyl, ethyl, n-propyl, isopropyl, n-butyl, isopentyl, n-hexyl, ethylhexyl, n-octyl and isooctyl, and a straight-chain chloroalkyl group having 1 to 3 carbon atoms such as chloromethyl and chloroethyl, among which hydrogen atom and methyl group are preferred.

The reactions for preparing a tribromoneopentyl chloroalkyl phosphate according to the present invention will be explained in detail.

First Step

An alkylene oxide of the formula (5) is reacted with phosphorus trichloride of the formula (4) in a chemical equivalent or less amount to the alkylene oxide to yield a tris(chloroalkyl) phosphite of the formula (1) as shown in the following reaction scheme (a):

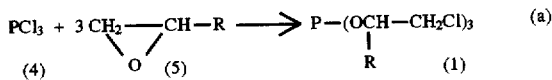

, wherein R is the same as defined above.

In the first step, the alkylene oxide may preferably be used in 3.0 to 3.6 moles, more preferably 3.0 to 3.3 moles, to 1.0 mole of phosphorus trichloride. The alkylene oxide may be used in such an excess amount for reducing the acid value of the product. When the alkylene oxide is used at a ratio smaller than 3.0 moles to 1.0 mole of phosphorus trichloride, undesired crystalline tris(tribromoneopentyl)alcohol and bis(tribromo-neopentyl)chloroalkyl phosphate will be generated in the last step. When the alkylene oxide is used at a ratio larger than 3.6 moles, the production efficiency will be decline disadvantageously.

Examples of usable alkylene oxides are those having 2 to 11 carbon atoms, such as epoxyethane, epoxypropane, epoxybutane, epoxymethylbutane, epoxypentane, epoxyhexane, epoxymethylhexane, epoxyheptane, epoxyethyloctane, epoxydecane, epoxymethyldecane, epichlorohydrin and chloroepoxybutane, among which epoxyethane and epoxypropane are preferred.

After the first step, an excess alkylene oxide if any may preferably be removed by evaporation in vacuo. The temperature for the removal may be within the range in which the phosphite does not decompose, preferably from 0° to 150° C., more preferably from 20° to 80° C. The pressure for the removal may preferably be 0.1 to 500 mmHg.

Second Step

Then, the resulting tris(chloroalkyl) phosphite is reacted with chlorine to obtain bis(chloroalkyl) phosphorochloridate as shown in the following reaction scheme (b). The formula (6) in the reaction scheme (b) represents an alkylene dichloride.

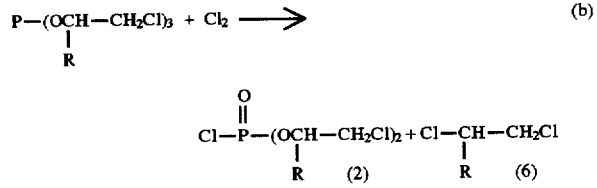

, wherein R is the same as defined above.

In the above-described second step, chlorine practically as chlorine gas may preferably be used in 1.0 to 1.5 moles, more preferably 1.0 to 1.2 moles, to 1.0 mole of the tris(chloroalkyl) phosphite. The reaction temperature in the second step may preferably be 0° to 150° C., more preferably 20° to 80° C. The reaction temperature lower than 0° C. is not preferable because sufficient reaction does not take place. On the other hand, the reaction temperature higher than 150° C. is not preferable because the tris(chloroalkyl) phosphite decomposes. In the second step, an amine compound such as triethylamine or tributhylamine, or a hydrin compound such as ethylene chlorohydrin or propylene chlorohydrin may be added as a stabilizer for the tris(chloroalkyl) phosphite. When carried out under the above-mentioned conditions, the second step will proceed in substantially quantitative.

Although the alkylene dichloride is generated in an equimolecular amount to the tris(chloroalkyl) phosphite, this compound can be removed by evaporation in vacuo. The alkylene dichloride may be removed at any stage after the second step, the third step or post-treatment. The temperature for the removal may preferably be 30° to 100° C., and the pressure may preferably be 0.1 to 500 mmHg. Since most alkylene dichlorides have relatively low boiling points, they can be removed at a temperature lower than 100° C. under a high vacuum pressure of 10 mmHg or less.

Third Step

Then, as shown in the following reaction scheme (c), the bis(chloroalkyl) phosphorochloridate is reacted with tribromoneopentyl alcohol of the formula (7) to prepare the tribromoneopentyl chloroalkyl phosphate of the formula (3):

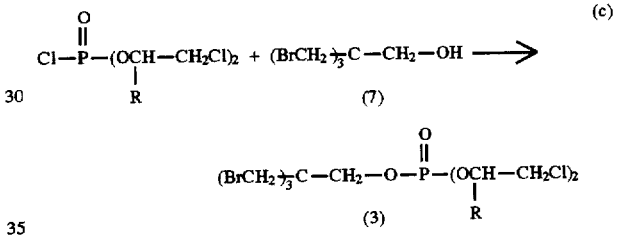

, wherein R is the same as defined above.

In the third step, tribromoneopentyl alcohol may preferably be used in 1.0 to 1.5 moles, more preferably 1.0 to 1.2 moles, to 1.0 mole of the bis(chloroalkyl) phosphorochloridate. The reaction temperature in the third step is preferable 40° to 150° C., more preferably 60° to 110° C. The reaction temperature lower than 40° C. is not preferable because sufficient reaction does not take place. On the other hand, the reaction temperature higher than 150° C. is not preferable because the intermediate bis(chloroalkyl) phosphorochloridate decomposes.

The third step may preferably be carried out in the presence of a Lewis acid catalyst. Examples of the Lewis acid catalysts are magnesium chloride, aluminum chloride and titanium tetrachloride. The use amount, for example, of aluminum chloride, may preferably be 2.5 to 60.0 millimoles, more preferably 5.0 to 50.0 millimoles, to 1.0 mole of tribromoneopenthyl alcohol.

The tribromoneopentyl chloroalkyl phosphate obtained in the third step contains little of the monomeric component, substantially having the purity of 100%.

In the preparation process of the present invention, hydrochloric acid is not generated and it is not necessary to use amines for removing hydrochoric acid. Therefore, the obtained tribromoneopentyl chloroalkyl phosphate does not contain any remaining amine which otherwise would adversely affect fogging characteristic when the product is used with polyurethanes.

The time period necessary for completing each of the reactions in the preparation process of the present invention is from 2 to 5 hours in industrial scale provided that the raw materials are economically used. For example, when the bis(chloroalkyl) phosphorochloridate of the formula (2) is reacted with an equimolar amount of tribromoneopentyl alcohol at a reaction temperature of 60° to 110° C., the reaction time for 2 to 4 hours is required for obtaining a tribromoneopentyl chloroalkyl phosphate with good quality.

After the above-described first to third steps, it may be preferable that the reaction mixture is discharged from a reactor and made into a finished product through washing and dehydration steps. The washing may be done by a conventional method, and both batch and continuous method may be used. For example, the reaction mixture is washed with an aqueous solution of mineral acid such as sulfuric acid and hydrochloric acid, followed by an alkali or water cleaning and dehydration under reduced pressure. Alternatively, the reaction mixture may be subjected to the alkali cleaning instead of being washed with the aqueous mineral acid solution, and, after removing by filtrating or centrifuging a water-insoluble aluminum compound (catalytic component), the reaction mixture may be washed with water and dehydrated under reduced pressure.

The tribromoneopentyl chloroalkyl phosphate obtained by the preparation process of the present invention can be suitably used as a flame-retardant for polyurethane foams. In this case, 0.1 to 60 parts by weight of the tribromoneopentyl chloroalkyl phosphate of the formula (3) may be used together with, if necessary, 0 to 40 parts by weight of a non-reactive organophosphorous compound acting as a flame-retardant plasticizer, 0 to 50 parts by weight of a bromohydrin compound of pentaerytiritol and 0 to 5 parts by weight of an antioxidant, with respect to 100 parts by weight of a polyol which is a material of a polyurethane foam.

Any polyol can be used provided that it is generally used as a material of polyurethanes, but aptly used are polyols such as polyester polyol and polyether polyol which have about 2 to 8 hydroxyl groups per molecule and a molecular weight of about 250 to about 6500. Polyols with a molecular weight of less than 250 are not suitable for forming polyurethane foams because of their great activity, and polyols with a molecular weight of more than 6500 damage workability because of their high viscosity.

Examples of the polyols are diols; triols; and polyols such as sorbitol, sucrose, or polyols obtained by polymerization of ethylene oxide and/or propylene oxide with an amine such as ethylenediamine as an initiator. Specific examples are diols such as polyoxyethylene glycol and polyoxypropylene glycol; triols such as polyoxyethylene glycerol, polyoxypropylene glycerol, poly(oxyethylene)poly(oxypropylene)glycerol, polyoxyethyleneneohexanetriol, polyoxypropylenepentaneohexanetriol,poly(oxyethylene) poly(oxypropylene)neohexanetriol,poly(oxypropylene)1,2,6-hexanetriol and polyoxypropylene alkanol, poly(oxyethylene)poly(oxypropylene)ethylenediamine; hexols such as polyoxyethylene sorbitol and polyoxypropylene sorbitol; octols such as polyoxyethylene sucrose and polyoxypropylene sucrose; and a mixture thereof. Also it is possible to use polyols, phosphorus-containing polyols or the like, commercially available as special grades, in which melamine or poly(ammonium phosphate) is dispersed. Preferred are polyether polyols such as poly(oxyethylene/oxypropylene)triols having an average molecular weight of about 250 to about 6500.

The flame-retardant plasticizer may preferably have an average molecular weight of 350 or more because a plasticizer having a small molecular weight tends to volatilize by heat. Examples thereof are tris(dichloropropyl) phosphate, Antiblaze 78 (chlorinated polyphosphonate manufactured by Albright & Wilson), Thermolin 101 [tetrakis(2-chloroethyl)- ethylene diphosphate manufactured by Olin Urethane Chemicals], Phosgard 2XC20 [2.2 bis-(chloromethyl)-1,3-propanebis(chloroethyl)-diphosphate manufactured by Monsanto Chemical Company], CR-530, CR-570 and CR-509 (halogen-containing phosphate phosphonate oligomer esters manufactured by Daihachi Chemical Industry Co., Ltd., CR-504 and CR-505 (halogen-containing diphosphate oligomer esters manufactured by Daihachi Chemical Industry Co., Ltd.), cresyl diphenyl phosphate and tricresyl phosphate.

The bromohydrin compounds of pentaerythritol are solid with a melting point. Examples thereof include dibromoneopentyl glycol and tribromoneopentyl alcohol.

Examples of the antioxidants include hydroquinone compounds of the formula (8):

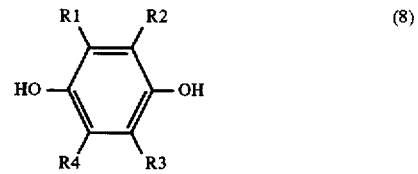

, wherein each of $R^1$, $R^2$, $R^3$ and $R^4$ represents hydrogen atom or a $C_{1-14}$ alkyl group, and/or trivalent organophosphorous compounds. Examples of the above-mentioned hydroquinone compounds include hydroquinone, 2,5-di-t-amylhydroquinone, 2,5-dioctylhydroquinone, t-amylhydroquinone, t-butyl-hydroquinone and octylhydroquinone. Especially, examples of hydroquinone compounds having excellent heat-resistance are 2,5-di-t-amylhydroquinone and 2,5-di-t-butylhydroquinone.

Examples of the above-mentioned trivalent organophosphorous compounds are triphenyl phosphite, tris(nonylphenyl) phosphite, diphenylisodecyl phosphite, tris(2,4-di-t-butylphenyl)pentaerythritol diphosphite, and tetrakis-(2,4-di-t-butylphenyl)-4,4-diphenylene phosphonite.

An exemplary method of producing a flame-retarded polyurethane foam using the tribromoneopentyl chloroalkyl phosphate of the present invention will be described. That is, polyurethane foam may be produced by adding the tribromoneopentyl chloroalkyl phosphate to the reaction of the polyol with toluenediisocyanate (TDI) in the presence of a catalyst, water or a blowing agent, a dispersant and the like, and then heating with stirring.

TDIs include isomers of 2,4- and 2,6-toluenediisocyanates and the concentration of these isomers preferably has an index of about 80 to about 120 for the 80/20 TDI, but not limited thereto.

As the catalyst, tertiary amine catalysts (e.g., triethylenediamine, dimethylethanolamine and N-ethylmorphohne) may be used, and as the blowing agent, compounds having a low-boiling point such as water, flurocarbon and methylene chloride may be used.

As the dispersant, nonionic surfactants such as ether-type, etherester-type and ester-type ones may be used. Examples are alkyl(methyl, ethyl, propyl, butyl, amyl, heptyl, octyl, nonyl, decyl, dodecyl, tridecyl)- and aryl(phenyl, tolyl, xylyl, biphenyl, naphlthyl)polyoxyethylene ethers, alkyl aryl formaldehyde-condensed polyoxyethylene ethers, polyoxyethylene ethers of glycerin esters, polyethylene glycol fatty acid esters, propylene glycol esters, polyglycerins, sorbitan esters, fatty acid monoglycerides and mixtures thereof.

To sum up, according to the present invention, it is possible to provide a tribromoneopentyl chloroalkyl phosphate which does not substantially contain monomeric and crystalline by-products, thereby exhibiting excellent workability and low fogging characteristic. The invention is constituted of the three steps of reacting an alkylene oxide with phosphorus trichloride in a chemical equivalent or less amount to the alkylene oxide to obtain a tris(chloroalkyl) phosphite, then reacting the tris(chloroalkyl) phosphite with chlorine to obtain a bis(chloroalkyl) phosphorochloridate, and reacting the bis(chloroalkyl) phosphoro-chloridate with tribromoneopentyl alcohol to prepare a tribromoneopentyl chloroalkyl phosphate.

That is to say, the present invention also provides a process for preparing flame-retardants for polyurethane foam which are capable of providing flame-retardancy, low fogging characteristic, good thermal stability and resistance to scorching.

Thus, since the tribromoneopentyl chloroalkyl phosphate prepared according to the present invention is excellent in flame-retardancy, low fogging characteristic, thermal stability and resistance to scorching, the tribromoneopentyl chloroalkyl phosphate can be used as a flame-retardant useful for providing articles having desirable properties for the automobile and furniture industries.

The present invention will be further described with reference to the following examples; however, these examples are intended to illustrate the invention and are not to be construed to limit the scope thereof.

In the following examples, % means wt % and chlorine % means a quantitative value of chlorine in P—Cl bond determined by potentiometric titration unless otherwise indicated.

EXAMPLE 1

(First Step)

In a one-liter four-necked flask provided with a stirrer, a thermometer and a condenser connected to a water scrubber, 137.5 g (1.0 mole) of phosphorus trichloride, 0.3 g (3.0 millimoles) of triethylamine and 0.2 g (2.5 millimoles) of ethylenechlorohydrin were charged. The flask was heated to 60° C. With maintaining this temperature, 138.6 g (3.2 moles) of epoxyethane were blown into the flask for about two hours, and then the temperature of 60° C. was maintained for an hour. With maintaining this temperature further for an hour, excess epoxyethane was removed at 10 mmHg. Tris(chloroethyl) phosphite, 267.3 g, was obtained in a 99% yield. The acid value thereof was 0.9 KOH mg/g.

(Second Step)

To tris(chloroethyl) phosphite thus obtained, 71.0 g (1.0 mole) of chlorine gas was blown at 20° C. in about an hour. This temperature was maintained further for an hour. Then, nitrogen gas was introduced to the system to remove chlorine gas. A mixture of monochloro-di(chloroethyl) phosphate and 1,2-dichloroethane, 337.6 g, was obtained and the percentage of chlorine was 10.3% while theoretically estimated percentage was 10.5%.

(Third Step)

To the mixture of monochlorodi(chloroethyl) phosphate and 1,2-dichloroethane thus obtained, 2.4 g (18.0 millimoles) of aluminum chloride were added and the resulting mixture was heated to 80° C. To this mixture, 324.7 g (1.0 mole) of tribromoneopentyl alcohol were added in an hour with maintaining the temperature and the resulting mixture was allowed to react for further three hours.

The resulting mixture was washed with an aqueous solution of soda ash (sodium carbonate) and the organic phase was separated from an aqueous phase. Then low-boiling point components and 1,2-dichloroethane were recovered by distillation in vacuo. Thus the object phosphate ester, 503 g, was obtained in a 95% yield. The resulting phosphate ester was found to be 100% tribromoneophentyl bis(chloroethyl) phosphate from area-ratio by gel permeation chromatography (GPC).

EXAMPLE 2

(First Step)

The procedure was the same as in Example 1 except that 182.7 g (3.2 moles) of epoxypropane was used instead of epoxyethane. Tris(chloropropyl) phosphite, 308.4g, was obtained in a 99% yield. The acid value thereof was 0.9 KOH mg/g.

(Second Step)

The second step was carried out in the same way as in Example 1. A mixture of monochlorodi(chloropropyl) phosphate and 1,2-dichloropropane, 378.7g, was obtained. The percentage of chlorine was 9.2%.

(Third Step)

The third step was carried out in the same way as in Example 1. The object phosphate ester, 535 g, was obtained in a 96% yield. The resulting phosphate ester was found to be 100% tribromoneophentyl bis(chloropropyl) phosphate from the area-ratio by GPC.

COMPARATIVE EXAMPLE 1

Synthesis from phosphorus oxychloride - 1

(First Step)

In a one-liter four-necked flask provided with a stirrer, a thermometer and a condenser connected to a water scrubber, 307.0 g (2.0 moles) of phosphorus oxychloride, 324.7 g (1.0 mole) of tribromoneopentyl alcohol and 0.3g (3.2 millimoles) of magnesium chloride were charged. This mixture was heated to 70° C. and allowed to react for 6 hours. After the reaction, generated hydrochloric acid and unreacted phosphorus oxychloride were removed at 70° C. under a reduced pressure of 5 mmHg for 2 hours. Then nitrogen gas was blown into the system at a flow rate of 5m³/hour under a reduced pressure of 20 mmHg for 2 hours. Thus an intermediate phosphate ester, 440 g, was obtained. The content of chlorine was 16.1%.

(Second Step)

To this intermediate, 0.4 g (2.3 millimoles) of titanium tetrachloride was added as a catalyst. The mixture was heated to 80° C.

With maintaining this temperature, 92.4 g (2.1 moles) of ethylene oxide was blown in about an hour. The resulting mixture was heated to 90° C. and then the temperature was maintained for an hour.

The resulting mixture was washed with an aqueous solution of soda ash and separated from an aqueous phase. Then low-boiling point components were recoverd in vacuo. Thus 503 g of phosphate ester was obtained.

In this Comparative Example 1, the yield was calculated with respect to 100 indicating that the starting material, tribromoneopentyl alcohol, is all made into the desired tribromoneopentyl bis(chloroalkyl) phosphate.

The generated compounds were found to be 95% tribromoneopentyl bis(chloroethyl) phosphate, 4% bis (tribromoneopentyl)chloroethylphosphate and 1% tris (chloroethyl) phosphate from the area-ratio by GPC.

COMPARATIVE EXAMPLE 2

Synthesis from phosphorus oxychloride - 2

The intermediate phosphate ester, 440 g, was obtained in the same way as in Comparative Example 1 except that the removal of hydrochloric acid and phosphorus oxychloride was carried out by thin film distillation. Tie percentage of chlorine was 16.1%.

To this intermediate, 0.4 g (2.3 millimoles) of titanium tetrachloride was added as a catalyst. The mixture was heated to 80° C. With maintaining this temperature, 121.8 g (2.1 moles) of propylene oxide was blown in an hour. The resulting mixture was heated to 90° C. and then the temperature was maintained for an hour.

The resulting mixture was treated in the same manner as described in Comparative Example 1. Thus 524 g of phosphate esters were obtained. The generated compounds were found to be 95% tribromo-neopentyl bis(chloropropyl) phosphate, 4% bis(tribromoneopentyl)-chloropropyl phosphate and 1% tris(cliloropropyl) phosphate from the area-ratio by GPC.

COMPARATIVE EXAMPLE 3

Synthesis according to U.S. Pat. No. 4,046,719

Into a flask, 500 g (1.5 moles) of tribromoneopentyl alcohol and 0.8 g of magnesium oxide were charged and heated to 60° C. Then 231.5 g (1.5 moles) of phosphorus oxychloride was added in 2 hours. The resulting mixture was heated to 138° C. The temperature was maintained for 3 hours while generated hydrochloric acid was removed. An intermediate phosphate ester, 674 g, was thus obtained. The percentage of chlorine was 16.2%. Next, this intermediate was cooled to 95° C. and the temperature was maintained at 92° C. for an hour under reflex. The acid value was then 0.12. Then the resulting substance was washed with an aqueous sodium hydroxide solution and the like. Thus 728 g of product was obtained.

The product was found to be 65% tribromoneopentyl bis(chloropropyl) phosphate, 20% bis(tribromoneopentyl) chloropropyl phosphate, 5% tris(tribromoneopentyl) phosphate and 10% tris(chloropropyl) phosphate from the area-ratio by GPC.

Table 1 shows the obtained compounds and the properties thereof in the above Examples 1 and 2, and Comparative Examples 1 to 3.

TABLE 1

| GPC Analysis | Example 1 | Example 2 | Comparative Example 1 | Comparative Example 2 | Comparative Example 3 |
|---|---|---|---|---|---|
| Compound A | 100 | — | 95 | — | — |
| Compound B | — | 100 | — | 95 | 65 |
| Compound C | — | — | 4 | — | — |
| Compound D | — | — | — | 4 | 20 |
| Compound E | — | — | — | — | 2 |
| Compound F | — | — | 1 | — | — |
| Compound G | — | — | — | 1 | 10 |
| Viscosity cps/25° C. | 700 | 1300 | 800 | 1700 | 4500 |
| Appearance | all being transparent liquid | | | | |

Compound A: Tribromoneopentyl bis(chloroethyl)phosphate
Compound B: Tribromoneopentyl bis(chloropropyl)phosphate
Compound C: Bis(tribromoneopentyl)chloroethyl phosphate
Compound D: Bis(tribromoneopentyl)chloropropyl phosphate
Compound E: Tris(tribromoneopentyl)phosphate
Compound F: Tris(chloroethyl)phosphate
Compound G: Tris(chloropropyl)phosphate Table 1 clearly shows that the tribromoneopentyl chloroalkyl phosphate can be obtained in a high purity by the method of the present invention.

EXAMPLE 3

Preparation of flame-retardant polyurethane foam of low fogging characteristic

Ingredients:

Polyol (polyether polyol manufactured by Mitsui Toatsu Chemicals, Inc., molecular weight: 3000): 100 parts Isocyanate (tolylenediisocyanate manufactured by Mitsui Toatsu Chemicals, Inc., 42.4/2,6 80/20): 59.5 parts Silicone oil (trade name: F-242T, manufactured by Shin-Etsu Chemical Co., Ltd.): 1.2 parts Tin-base catalyst (trade name: STANN BL, manufactured by Sankyo Organic Chemicals Co., Ltd.): 0.3 parts Amine-base catalyst (trade name : Kaolizer NO. 1, manufactured by Kao Corporation): 0. 1 parts Water: 4.5 parts Methylene chloride: necessary parts Flame-retardant (tribromoneopentyl chloroalkyl phosphate): necessary parts Flexible urethane foams were prepared according to the above recipe by a one-shot process.

The polyol, silicone oil, catalyst, water and flame-retardant were blended in the amount as described in the above recipe and homogeneously mixed by stirring at 3000 r.p.m. for 1 minute. Then isocyanate was added and, after further stirring at 3000 r.p.m. for 5 to 7 seconds, the mixture was quickly poured into a cubic carton. Expansion was immediately observed and reached the maximum volume in several minutes. This substance was allowed to cure in an oven at 80° C. for 30 minutes. The obtained foams had a flexible white cellular structure.

Since, according to the preparation process of the present invention, the tribromoneopentyl chloroalkyl phosphate of an extremely high purity can be produced, volatile by-products such as free halogen are generated in much smaller amount and the resistance to hydrolysis of the product is more excellent, compared with the prior processes. The product is capable of providing flame retardancy, low fogging characteristic, scorch resistance and heat-discoloration resistance to polyurethane foam when used with the polyurethane foam.

Further, since the amount of crystalline components, i.e., bis(tribromoneopentyl)chloroalkyl phosphate and tris(tribromoneopentyl) phosphate, is very small in the product, it is possible to obtain a flame-retardant of low viscosity and of good workability.

What is claimed is:

1. A process of preparing a tribromoneopentyl chloroalkyl phosphate of the formula (3):

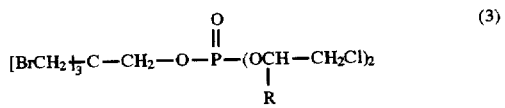

wherein R is hydrogen atom, an alkyl or chloroalkyl group, comprising:

a first step of reacting an alkylene oxide with phosphorus trichloride in a chemical equivalent or less amount to the alkylene oxide to obtain a tris(chloroalkyl) phosphite of the formula (1):

wherein R is the same as defined above;

a second step of reacting the tris(chloroalkyl) phosphite with chlorine to obtain a bis(chloroalkyl) phosphorochloridate of the formula (2):

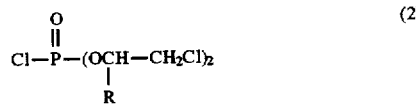

wherein R is the same as defined above; and a third step of reacting the bis(chloroalkyl) phosphorochloridate with tribromoneopentyl alcohol.

2. The process according to claim 1 wherein the substituent R is hydrogen atom, a straight-chain or branched-chain alkyl group having 1 to 10 carbon atoms, or a straight chain chloroalkyl group having 1 to 3 carbon atoms.

3. The process according to claim 2 wherein the substituent R is hydrogen atom or methyl group.

4. The process according to claim 1 wherein the alkylene oxide is epoxyethane, epoxypropane, epoxybutane, epoxymethylbutane, epoxypentane, epoxyhexane, epoxymethylhexane, epoxyheptane, epoxyethyloctane, epoxydecane, epoxymethyldecane, epichlorohydrin or chloroepoxybutane.

5. The process according to claim 4 wherein the alkylene oxide is epoxyethane or epoxypropane.

6. The process according to claim 1 wherein the molar ratio of phosphorus trichloride to the alkylene oxide is 1.0:3.0 to 3.6.

7. The process according to claim 6 wherein the molar ratio of phosphorus trichloride to the alkylene oxide is 1.0:3.0 to 3.3.

8. The process according to claim 1 wherein, after the first step, an excess of the alkylene oxide is removed by evaporation at a temperature of 20° to 80° C. under a reduced pressure of 0.1 to 500 mmHg.

9. The process according to claim 1 wherein the molar ratio of the tris(chloroalkyl) phosphite to chlorine is 1.0:1.0 to 1.5.

10. The process according to claim 9 wherein the molar ratio of the tris(chloroalkyl) phosphite to chlorine is 1.0:1.0 to 1.2.

11. The process according to claim 1 wherein the second step is carried out at a temperature of 0° to 150° C.

12. The process according to claim 11 wherein the second step is carried out at a temperature of 20° to 80° C.

13. The process according to claim 1 wherein the second step is carried out in the presence of a stabilizer selected from triethylamine, tributylamine, ethylene chlorohydrin and propylene chlorohydrin.

14. The process according to claim 1 wherein, after the second or third step, an alkylene dichloride generated in the second step is removed by evaporation at a temperature within the range of 30° to 100° C. under a pressure within the range of 0.1 to 500 mmHg.

15. The process according to claim 1 wherein the molar ratio of the bis(chloroalkyl) phosphorochloridate to tribromoneopentyl alcohol is 1.0:1.0 to 1.5.

16. The process according to claim 15 wherein the molar ratio of the bis(chloroalkyl) phosphorochloridate to tribromoneopentyl alcohol is 1.0:1.0 to 1.2.

17. The process according to claim 1 wherein the third step is carried out at a temperature of 40° to 150° C.

18. The process according to claim 17 wherein the third step is carried out at a temperature of 60° to 110° C.

19. The process according to claim 1 wherein the third step is carried out in the presence of a Lewis acid catalyst selected from magnesium chloride, aluminum chloride and titanium tetrachloride.

20. The process according to claim 1 wherein the third step is carried out in the presence of 5.0 to 50.0 millimoles of aluminum chloride as a Lewis acid catalyst to 1.0 mole of tribromoneopentyl alcohol.

* * * * *

UNITED STATES PATENT AND TRADEMARK OFFICE
CERTIFICATE OF CORRECTION

PATENT NO. : 5,756,797
DATED : May 26, 1998
INVENTOR(S) : N. MIYANO et al.

Page 1 of 4

It is certified that error appears in the above-identified patent and that said Letters Patent is hereby corrected as shown below:

At column 1, line 14 of the printed patent, change "they" to ---polyurethane foams---.
At column 1, line 18 of the printed patent, change "products" to ---products,---.
At column 1, line 18 of the printed patent, change "parts" to ---parts,---.
At column 1, line 26 of the printed patent, delete "the".
At column 1, line 36 of the printed patent, change "provided by" to ---disclosed in---.
At column 1, line 47 of the printed patent, delete "the".
At column 1, line 52 of the printed patent, change "On the other hand" to ---Additionally---.
At column 1, line 54 of the printed patent, delete "the".
At column 1, line 65 of the printed patent, change ". And" to ---, with---.
At column 1, line 65 of the printed patent, change "is" to ---being---.
At column 2, line 13 of the printed patent, change "Nor is" to ---Moreover,---.
At column 2, line 14 of the printed patent, after "phosphates" insert ---is not---.

UNITED STATES PATENT AND TRADEMARK OFFICE
CERTIFICATE OF CORRECTION

PATENT NO.   : 5,756,797    Page 2 of 4
DATED        : May 26, 1998
INVENTOR(S)  : N. MIYANO et al.

It is certified that error appears in the above-identified patent and that said Letters Patent is hereby corrected as shown below:

At column 2, line 15 of the printed patent, change "are" to ---is---.
At column 3, line 33 of the printed patent, change "be decline disadvantageously" to ---disadvantageously decline---.
At column 4, line 1 of the printed patent, change "The" to ---A---.
At column 4, line 3 of the printed patent, change "the" to ---a---.
At column 4, line 11 of the printed patent, change "in substantially quantitative" to ---substantially quantitatively---.
At column 4, line 42 of the printed patent, change "The" to ---A---.
At column 4, line 45 of the printed patent, change "the" to ---a---. ( second occurence )
At column 5, line 11 of the printed patent, change "method" to ---methods---.
At column 5, line 16 of the printed patent, change "the" (second occurrence) to ---an---.
At column 7, line 39 of the printed patent, change "With" to ---While---.
At column 7, line 42 of the printed patent, change "With" to ---While---.
At column 7, line 54 of the printed patent, after "while" insert ---the---.

UNITED STATES PATENT AND TRADEMARK OFFICE
CERTIFICATE OF CORRECTION

PATENT NO. : 5,756,797  Page 3 of 4
DATED : May 26, 1998
INVENTOR(S) : N. MIYANO et al.

It is certified that error appears in the above-identified patent and that said Letters Patent is hereby corrected as shown below:

At column 7, line 63 of the printed patent, change "with" to ---while---.

At column 11, line 18 (claim 1, line 6) of the printed patent, change "a first step of" to ---first,---.

At column 11, line 27 (claim 1, line 12) of the printed patent, change "a second step of" to ---second,---.

At column 11, line 37 (claim 1, line 17) of the printed patent, change "a third step of" to ---third,---.

At column 12, line 9 (claim 8, line 2) of the printed patent, change "step" to ---reaction---.

At column 12, line 19 (claim 11, line 2) of the printed patent, change "step" to ---reaction---.

At column 12, line 21 (claim 12, line 2) of the printed patent, change "step" to ---reaction---.

At column 12, line 24 (claim 13, line 2) of the printed patent, change "step" to ---reaction---.

At column 12, line 28 (claim 14, line 2) of the printed patent, change "step" to ---reaction---.

UNITED STATES PATENT AND TRADEMARK OFFICE
CERTIFICATE OF CORRECTION

PATENT NO. : 5,756,797
DATED : May 26, 1998
INVENTOR(S) : N. MIYANO et al.

It is certified that error appears in the above-identified patent and that said Letters Patent is hereby corrected as shown below:

At column 12, line 29 (claim 14, line 3) of the printed patent, change "step" to ---reaction---.

At column 12, line 39 (claim 17, line 2) of the printed patent, change "step" to ---reaction---.

At column 12, line 41 (claim 18, line 2) of the printed patent, change "step" to ---reaction---.

At column 12, line 43 (claim 19, line 2) of the printed patent, change "step" to ---reaction---.

At column 12, line 44 (claim 19, line 3) of the printed patent, change "from magnesium" to ---from the group consisting of magnesium---.

At column 12, line 48 (claim 20, line 2) of the printed patent, change "step" to ---reaction---.

Signed and Sealed this

Twenty-fifth Day of May, 1999

Attest:

Q. TODD DICKINSON

*Attesting Officer*      *Acting Commissioner of Patents and Trademarks*